United States Patent
Herdzik et al.

(10) Patent No.: US 8,161,804 B2
(45) Date of Patent: Apr. 24, 2012

(54) APPARATUS AND METHODS FOR MAINTAINING PROPER TEST PIECE ORIENTATION DURING CORROSION TESTING

(75) Inventors: Nicholas Philip Herdzik, Sterling Heights, MI (US); Andrew Raymond Nowasielski, Shelby Township, MI (US); Adam Richard Muehlhauser, Ypsilanti, MI (US); Janet Christine Robincheck, Sterling Heights, MI (US); Jerry Walter Slumski, Flat Rock, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 332 days.

(21) Appl. No.: 12/480,274

(22) Filed: Jun. 8, 2009

(65) Prior Publication Data

US 2010/0307229 A1 Dec. 9, 2010

(51) Int. Cl.
*G01N 17/00* (2006.01)
(52) U.S. Cl. .......................................................... 73/86
(58) Field of Classification Search .............. 73/86, 431, 73/866.5; 204/404; 324/71.2
See application file for complete search history.

(56) References Cited

U.S. PATENT DOCUMENTS

| | | | |
|---|---|---|---|
| 3,957,440 A * | 5/1976 | Aussieker | 422/53 |
| 4,092,122 A * | 5/1978 | Suga | 422/53 |
| 4,309,899 A | 1/1982 | Torres | |
| 4,594,487 A * | 6/1986 | Grassl et al. | 200/82 E |
| 4,697,465 A | 10/1987 | Evans et al. | |
| 5,415,047 A * | 5/1995 | Maciejewski et al. | 73/850 |
| 5,811,686 A * | 9/1998 | Lavoie et al. | 73/821 |
| 6,127,835 A * | 10/2000 | Kocher et al. | 324/750.25 |
| 6,918,306 B1 * | 7/2005 | Cavallaro et al. | 73/849 |
| 7,096,721 B2 * | 8/2006 | Bennett | 73/86 |
| 7,647,821 B2 * | 1/2010 | Bloomquist et al. | 73/86 |

* cited by examiner

*Primary Examiner* — Lisa Caputo
*Assistant Examiner* — Octavia Davis-Hollington
(74) *Attorney, Agent, or Firm* — Gifford, Krass, Sprinkle, Anderson & Citkowski, P.C.

(57) ABSTRACT

A support stand for supporting a test piece within a corrosion chamber comprises first and second side members interconnected by first and second support rods. The relative position of the support rods is adjustable so as to modify the orientation of the test piece. In some examples, each side member has a base, a first row of spaced-apart holes generally parallel to the base, and a second row of spaced apart holes generally perpendicular to the base. By selecting the holes with which the support rods engage, the orientation of the test piece can be set to a predetermined value.

10 Claims, 3 Drawing Sheets

APPARATUS AND METHODS FOR MAINTAINING PROPER TEST PIECE ORIENTATION DURING CORROSION TESTING

FIELD OF THE INVENTION

The present invention relates to improved apparatus and methods related to corrosion testing.

BACKGROUND OF THE INVENTION

Corrosion testing is used to evaluate test pieces such as metal panel. Typically, the corrosion properties of the test piece are evaluated when exposed to aqueous media such as water, saline solution, mild acids, and the like. Typically, larger test pieces, such as vehicle panels, are leaned against the wall of the corrosion chamber.

SUMMARY OF THE INVENTION

Examples of the present invention include improved methods and apparatus for corrosion testing. An example support stand for supporting a test piece within a corrosion chamber comprises first and second side members interconnected by first and second support rods. The relative positions of the support rods are adjustable so as to modify the orientation of a test piece supported by the support stand.

In some examples, each side member has a base, a first row of spaced-apart holes generally parallel to the base, and a second row of spaced apart holes generally perpendicular to the base (i.e., vertical). By selecting the holes with which the support rods engage, the orientation of the test piece can be set to a predetermined value.

The side members may have a generally L-shaped form having a first arm and a second arm, the first arm providing a base and providing the first row of spaced-apart holes therein. The holes may be uniformly spaced, though this is not necessary. The second aim provides the second row of spaced-apart holes. In use, two such side members may be spaced apart and interconnected by the support rods. The holes may be in positional register (for example, if the side pieces are of similar form), and oriented in the same direction, so that a support rod may extend through corresponding holes in each side member. Support rods of selectable lengths may be selected to modify the distance between the side members. The support rods may be generally horizontal when the side members rest on their base.

Components of the support stand, such as the side members, support rods, and any fasteners may be formed from a corrosion-resistant material, such as a corrosion-resistant metal, plastic, glass, ceramic or other material. In some examples, the side members and support rods are formed from a transparent material such as a transparent plastic, to facilitate inspection of parts.

The support stand can be reconfigured by disengaging the support rods from the side members, and reassembling the apparatus to provide a desired test angle. The relative positions of the first and second rod may be adjustable by selection of holes through which the support rods extend. The selected holes through which the support rods extend can be selectable so as to adjust the position of a supported test piece.

The relative positions of the support rods may be adjustable so as to support a test panel or other test piece at an angle of approximately 30 degrees to the vertical. The support rod may be solid or tubular.

A method of corrosion testing a test piece within a corrosion chamber comprises providing a support stand within the corrosion chamber, the support stand including a pair of side members, a first support rod, and a second support rod, the support rods extending between the pair of side members, at least one support rod having an adjustable position, placing the test piece on the support stand, the adjustable position being selected so that the test surface has a predetermined test angle, and corrosion testing the test piece with the test surface at the predetermined test angle. Each of the pair of side members may be generally L-shaped, and the side members and support rods can be formed from a corrosion-resistant material.

DETAILED DESCRIPTION OF THE INVENTION

Examples of the present invention include methods and apparatus for maintaining proper test piece orientation during corrosion performance testing.

An example apparatus comprises two side members formed from corrosion resistant material configured to hold corrosion resistant support rods. The support rods are elongate members, and are configured in such a manner to support the test surface at a desired angle.

An example apparatus allow a test piece to be placed in a corrosion chamber and positioned in a manner so that a test surface is maintained at a predetermined test angle. The test angle may be, for example, approximately 30° from the vertical.

In some examples, the side members are in the shape of the letter "L". In use, the side members are oriented so that one arm of the "L" is generally horizontal and provides the base, and the other arm is generally vertical. Each arm has a plurality of spaced-apart holes formed therethrough, in a direction normal to the plane of the "L". A pair of such side members can be placed so that they are in positional register. A first support rod can be placed extending between the horizontal arms, and a second support rod can be placed extending between holes in the vertical arms. The holes may have a diameter at least large enough to receive the support rods.

A first support rod may be placed at an appropriate horizontal position, for example using selected holes formed in the horizontal arms of the L-shaped side members. A second support rod may be placed at an appropriate height, for example being located between (and supported by) selected holes faulted in the vertical arms of the L-shaped side members. With appropriate choice of height and horizontal position of the support rods, the support rods are operable to support a test piece (sometimes referred to herein as a part) at a desired angle during corrosion testing.

Figure 1:
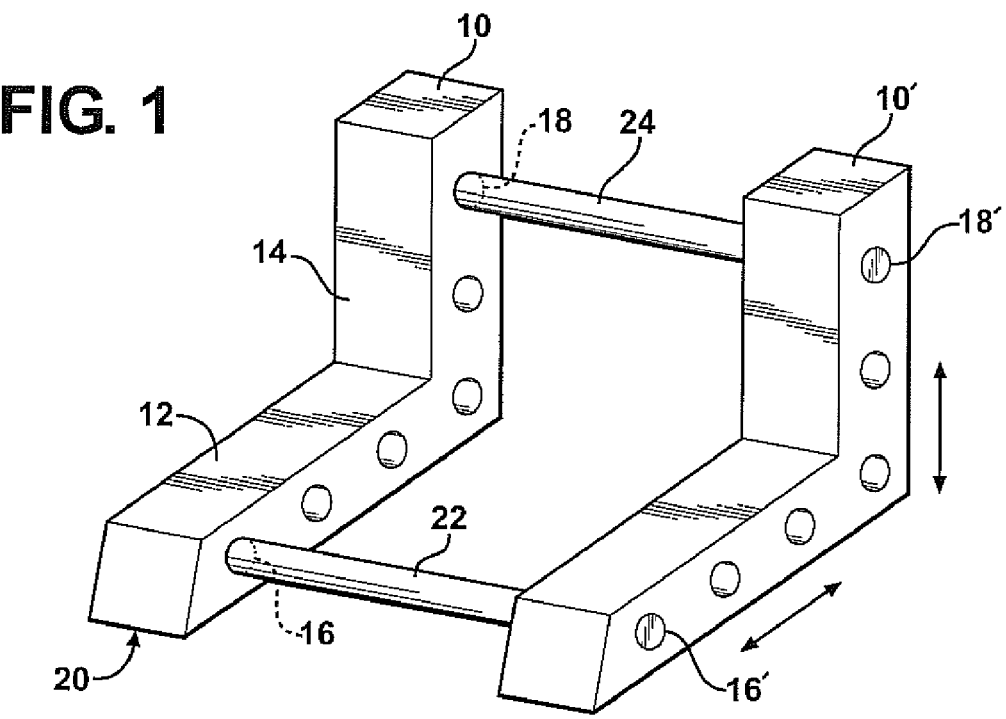
FIG. 1 shows a support stand according to an example of the present invention.

FIG. 1 shows a support stand according to an example of the present invention. The support stand comprises a pair of similar side members, labeled 10 and 10'. Each side member is generally "L" shaped and comprises a generally horizontal arm 12, which provides the base, and a generally vertical arm 14. The horizontal arm 12 has a generally horizontal row of holes formed therein, such as the hole 16. The vertical arm has a generally vertical row of holes formed therein, such as hole 18.

A first support rod 22 extends generally horizontally from hole 16 to corresponding hole 16' in the second side member 10'. A second support rod 24 extends generally horizontally from hole 18 to corresponding hole 18' in the second side member.

Figure 2:
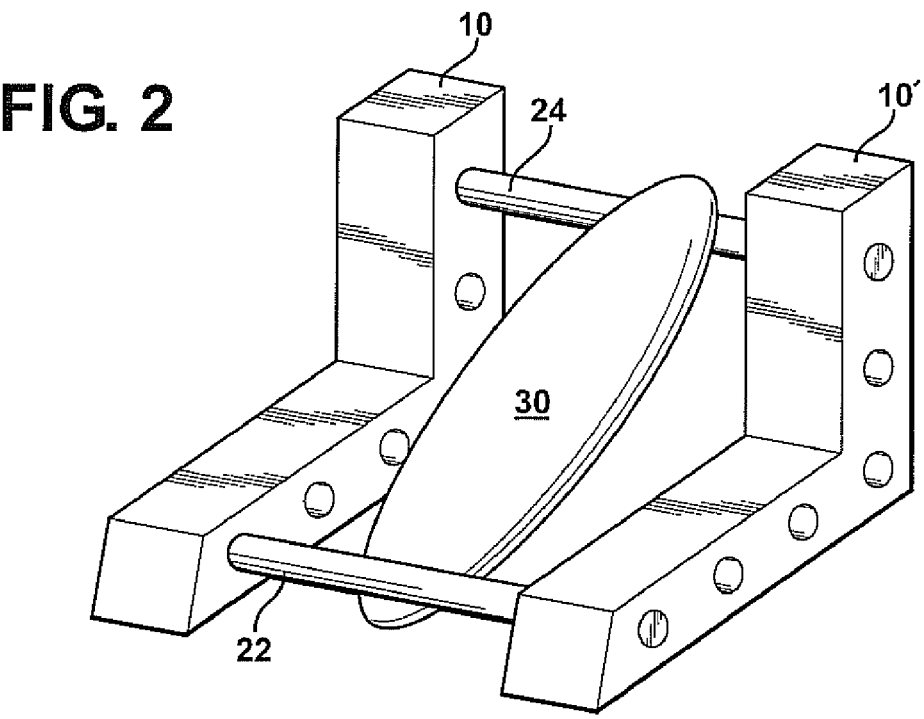
FIG. 2 shows the support stand of FIG. 1 supporting a test piece.

FIG. 2 shows the support stand of FIG. 1 supporting a test piece 30. The general orientation of the test piece 30 can be adjusted by moving the support rod 22 to a different horizontal position, and/or the second support rod 24 to a different vertical position.

Figure 3:
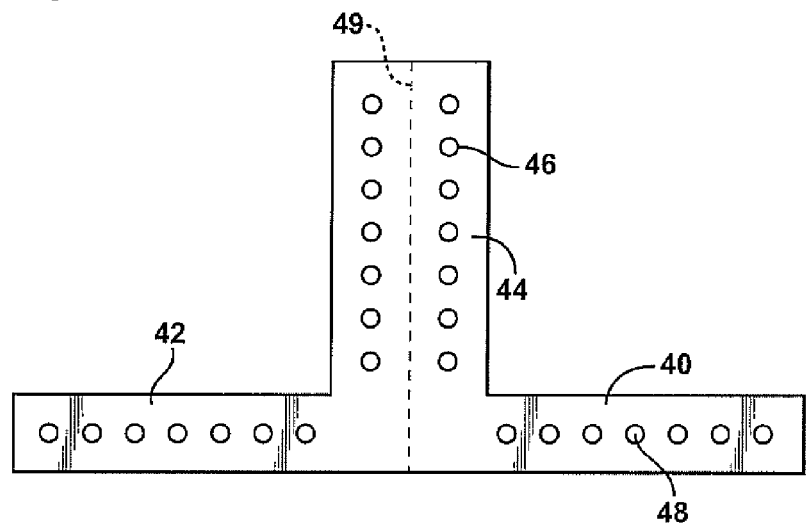
FIG. 3 shows another example of a support stand.

FIG. 3 shows another example of a support stand. In this example, the support stand has the general form of an inverted "T", with the top of the "T" forming the base. The apparatus comprises horizontal arms 40 and 42, a vertical arm 44, and hole arrangements 46 (vertical row) and 48 (horizontal row). This configuration may be formed by attaching two support stands of FIG. 1 in a back-to-back arrangement, e.g. along optional join line 49.

Figure 4:
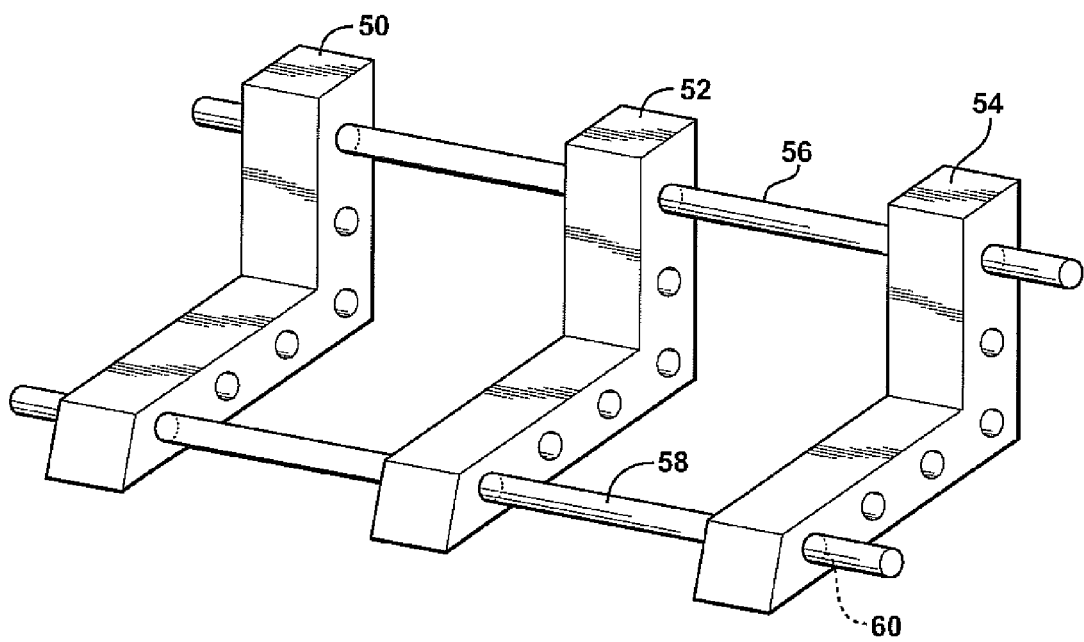
FIG. 4 shows a multiple side-by-side configuration.

FIG. 4 shows a multiple side-by-side configuration. Here, three L-shaped side members 50, 52, and 54 are arranged in a side-by-side spaced apart arrangement. The spacing may be non-uniform if desired. More than three side members may be arranged in this fashion. In this example, support rods 56 and 58, through holes such as 60, are used. However, in other examples a different support rod may be used to span each spaced apart gap between side members.

Figure 5:
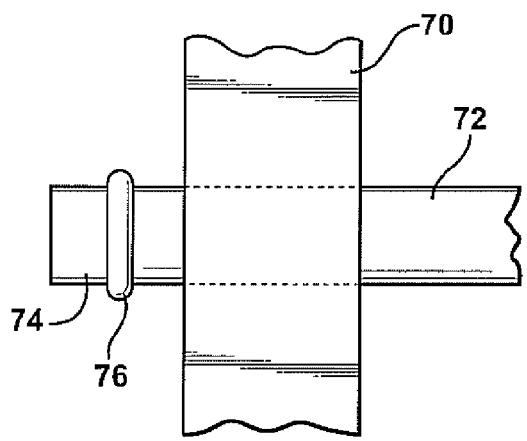
FIGS. 5 and 6 show a support rod extending through a hole in a portion of a side member.

FIG. 5 shows a support rod extending through a hole, being a view of a side member portion 70, with a support rod extending through a hole (not shown separately). A gasket 76 is pushed over the protruding end 74 of the support rod. Other attachments, clips, and the like may be used.

Figure 6:
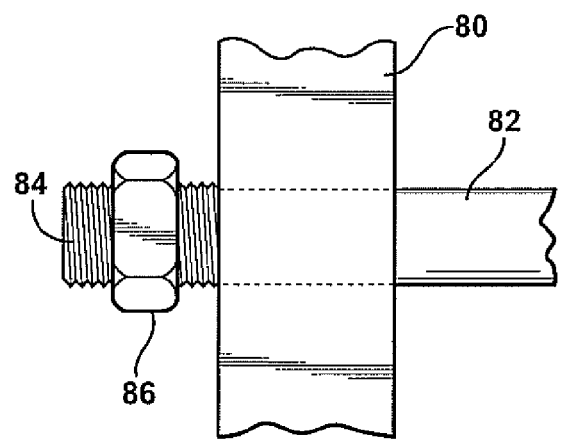

FIG. 6 also shows a support rod 82 extending through a hole in the side member 80, with a nut 86 screwed onto a threaded end portion 84. Other configurations are discussed further elsewhere.

Figure 7:
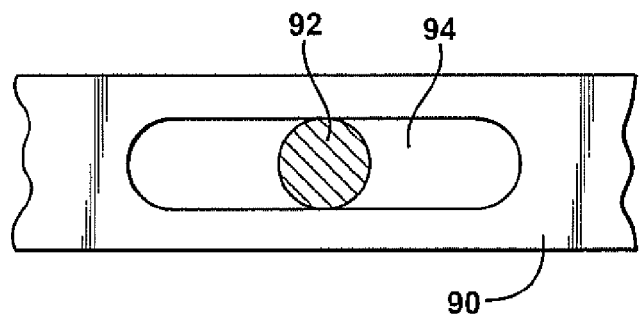
FIG. 7 shows a support rod extending through a slot-like hole.

FIG. 7 shows a support rod 92 extending through a slot-like hole 94 in a side member 90. The location of the support rod in the slot-like hole may be adjusted and secured, e.g. with one or more nuts. This approach allows relatively fine adjustment of the test angle without removing the support rod from the side member.

Corrosion Testing

During corrosion testing of a test piece, such as a vehicle panel or other component, the surface of the test piece may be scribed or otherwise damaged before the corrosion test. The test piece is then placed into a corrosion chamber.

A test piece may be simply leaned against a side wall of the chamber. However, placing test pieces against the wall of the corrosion chamber is not an efficient use of space, and the available wall space may be used up well before the chamber is filled. It may be difficult to achieve a desired test angle by resting the part against the chamber wall, depending on the geometry of the part. If not securely positioned, the part may slip out of position due to the presence of moisture inside the corrosion chamber. There may also be problems of spray non-uniformity near a wall. Hence, it is advantageous to provide a support stand to support test pieces, allowing the entire floor area of the corrosion chamber to be used, and avoiding other problems.

A corrosion test may include scratching or otherwise damaging a corrosion resistant layer, and may include monitoring corrosion of the test piece where the corrosion resistant layer is compromised. A corrosion test may be a salt-spray test (SST), a cyclic corrosion test (CCT), or other corrosion test.

A mist of droplets, such as saline water droplets, may be sprayed within the corrosion chamber. For a test angle (relative to the vertical) of 90°, liquid tends to accumulate on the flat surface and the results may be accelerated to an unpredictable degree. For a test angle of zero degrees (relative to the vertical), relatively few droplets may access the test surface and the corrosion may be too slow. The salinity, pH, droplet concentration, initial droplet size distribution, temperature, location of mist inlets, droplet inlet speed, and other corrosion test parameters may be controlled with predetermined value ranges if desired.

A predetermined test angle in the range 15°-45° degrees, such as 25°-35° and in particular approximately 30°, allows corrosion to be evaluated on reasonable time scales. In some examples, the test angle may be in the range of 20°-40° from the vertical.

The present inventors realized that lack of reproducible test angles may reduce test reliability. The support stands of an example invention can be readily configured to give improved control of the test angle for test pieces of varied size and geometry. Reproducibility of corrosion test results is enhanced using examples of the present invention, improving evaluation test pieces, allowing smaller changes to be detected, and possibly allowing the number of required corrosion tests to be reduced, compared to conventional approaches.

The orientation angle of the test surface at the monitored location, such as the location of the scratch or other damage, may be referred to as the test angle. The test angle may be defined in a corrosion test specification. Examples of the present invention allow the test angle to be more readily adjusted, and reproducible. The test angle can be better controlled and with improved reproducibility from one test to another.

A test piece may be a metal component, such as a metal panel or other test piece. The test piece may be coated with a corrosion resistant layer, such as plating, one or more paint layers, oxide layer, or other corrosion resistant layer. Example test pieces include vehicle components such as body panels, attachment fixtures, fasteners, and the like. A paint layer may be scratched before a corrosion test. A plated layer may be evaluated in an unscratched state.

Examples of the present invention include improved methods of corrosion testing relatively large test pieces, such a test piece having at least one dimension greater than 1 meter. Examples of the present invention include improved methods of corrosion testing a vehicle panel, such as an automobile panel.

Configuration of an Example Support Stand

Examples of the present invention allow test pieces, including larger parts such as vehicle panels, to be securely placed anywhere in the corrosion chamber while maintaining the desired test angle. The test angle may be approximately 30° from vertical. Using examples of the present invention, test pieces need not be placed against the wall of the chamber. Because the part is placed in an adjustable support stand with a plurality of contact points, it is relatively easy to achieve the desired test angle. There is also less chance for the part to accidentally fall out of the correct testing position.

In one example, an apparatus comprises two side members, each in the shape of the letter "L". Each side member has spaced-apart holes formed through them at a diameter large enough to accept the support rods. In other examples, a side member may be generally rectangular, with a first row of holes generally parallel to a longer side (which may be the generally horizontal row), and a second row of holes generally parallel to a shorter side (which may be the generally vertical row).

One support rod can be placed at the appropriate height by selecting appropriate holes from the vertical row of holes of each support, and the rod used to connect the two side members together. For an L-shaped side member, this corresponds to selecting holes corresponding to a desired vertical direction along the vertical support arm. This support rod creates one contact point for the part to rest against to achieve a desired test angle, for example approximately 30° from vertical. For L-shaped side members, the rod interconnects the vertical arms of spaced apart side members.

A second support rod can be placed at the appropriate distance along the horizontal support arm of each side member (for an L-shaped side member) and used to connect the two supports together. This support rod creates a second contact point for the part to rest against, to achieve the desired test angle.

By varying the height of the rod on the vertical support arm and the distance of the rod along the horizontal support arm, a variety of test piece shapes and structures can be securely positioned in a manner that allows them to be tested according to any specification or protocol.

The test angle (from the vertical) may be approximately the arctangent of the horizontal separation of the support rods divided by the vertical separation. The test angle may be modified by the local curvature of a test piece. However, the test angle can be adjusted by changing the vertical separation and/or the horizontal separation of the support rods, for example by selecting or changing the holes with which the support rods engage, or otherwise modifying the locations at which the support rods engage the side pieces.

Varying the location of the support rods allows a variety of test piece shapes to be held in a position that maintains the appropriate testing angle, while greatly reducing the risk of a test piece falling over. Test pieces can be placed in any area of the chamber during testing, and are not limited to being placed against a chamber wall.

Further Aspects of Example Apparatus

The support rod may be a generally elongate member, for example a dowel rod (a solid uniform elongate cylinder). The support rods may be generally cylindrical (solid or tubular). Support rods may extend through the selected holes and out of the other side of the side member. This may be sufficient engagement for practical use. However, clips, other fasteners, notches, ribs, or other forms may be used to assist positioning and engagement of the support rods and the holes. End portions of the support rods may be threaded or have a region of reduced diameter, and in some examples may be tapered, e.g. to facilitate frictional engagement with a selected hole.

The side members may be spaced apart a distance that is approximately equal to the length of the support rod, minus the length of support rod that extends into and through the selected hole in the side members. The spacing between the side members may be adjusted through selection of a support rod length from a plurality of available support rod lengths.

The holes may be evenly spaced in a row, spaced so as to obtain uniform orientation angle increments, or otherwise spaced apart. A row of holes may be exactly linear, but in some examples there may be some positional non-linearity such as a curvature. The holes may extend through a side piece, but in some examples may not and may be in the form of depressions.

Holes may be circular, having a diameter similar to the outside diameter of the support rods. However, other shapes may be used, and a non-circular hole profile may match a non-circular support rod profile. For example, holes may be square, rectangular, oval, hexagonal, or other geometric shape. In some examples, holes may be interconnected with a slot so that a support rod can be moved from one hole to another without removal, possibly after reorientation of the support rod.

Support rods can be placed in various selectable positions along vertical and horizontal directions structural supports. A test piece is able to Jean against the upper support rod at the appropriate test angle, while being held in place by a lower support rod.

A side member may have a first arrangement of holes disposed parallel to and proximate to the base of the side member, and a second arrangement of apertures disposed generally vertically.

A support rod may engage an aperture in the side member by one or more of the following: pushing through the hole, frictional engagement, a snap connection, a threaded engagement, and the like. A support rod may protrude through the side member, and may be secured in place by a fastener such as a nut (such as a wing-nut), clip, gasket (such as rubber gasket), snap connection, and the like. Fasteners may be corrosion-resistant, for example plastic. A fastener may be provided on the support rod on each side of the side member. The support rod may be threaded, for example on an end portion thereof, and the threaded portion used to engage a threaded hole, a fastener such as a nut on one or both sides of the hole.

In some examples, support rods may include spring-loaded clips or other mechanisms to facilitate engagement with the selected holes.

The side members and/or support rods may be formed from a corrosion-resistant material, such as a plastic. In some examples, the side members and/or support rods may comprise a transparent plastic, such as an acrylic polymer such as poly(methyl methacrylate) (Plexiglas), or other polymer. Other corrosion resistant materials can be used for some or all of the assembly, such as the side members and/or support rods, including other polymers, glass, ceramic, wood, composites, or corrosion-resistant metal (such as stainless steel, brass, and the like).

The side members and/or support rods may have a uniform composition, for example the support rod may be a solid cylindrical or uniform tubular piece formed from a corrosion-resistant material. In some examples, side members and/or support rods are corrosion resistant due to a surface coating, for example a metal (such as steel) coated with a corrosion-resistant layer. Examples include rubberized metal, plastic coated metal, painted metal, or otherwise coated metal.

In some cases, support stands can be attached to each other, for example attached back-to-back or other arrangements. For example, support stands may be attached back to back with vertical arms connected together. Support stands may be attached together in different configurations. An example support stand comprises a side member having a one or more vertical arms supported by a generally planar horizontal base member.

Hence, an example support stand comprises a first side member, a second side member which may have the same general form as the first member and which may be identical to the first member, a first support rod, and a second support rod. The side members may be generally similar and in the same orientation, and spaced apart in a generally horizontal direction when in use. Each side member has a base configured to rest on the floor of a corrosion chamber, a first row of spaced-apart holes generally parallel to the base, and a second row of spaced apart holes generally perpendicular to the base. A support rod extending between holes selected from the first row of spaced-apart holes for each side member, and another support rod extends between holes selected from the second row of spaced-apart holes for each side member. A corrosion chamber may have a grate to allow liquids to flow away, and the base may be shaped to engage the grate pattern to prevent slippage. The base may support an anti-slip layer, which may include a powdered abrasive or similar material.

The invention is not restricted to the illustrative examples described above. Examples described are exemplary, and are not intended to limit the scope of the invention. Changes therein, other combinations of elements, and other uses will occur to those skilled in the art. The scope of the invention is defined by the scope of the claims.

Having described the invention, we claim:

1. An apparatus, the apparatus being a support stand for supporting a test piece within a corrosion chamber, the apparatus comprising:
   a first side member;
   a second side member;
   a first support rod; and
   a second support rod,
   each side member having a base, a first row of spaced-apart holes generally parallel to the base, and a second row of spaced apart holes generally perpendicular to the base,
   the first and second side members being spaced apart and connected by the support rods,
   the first support rod extending between holes selected from the first row of spaced-apart holes for each side member,
   the second support rod extending between holes selected from the second row of spaced-apart holes for each side member,
   each side member having a generally L-shaped form having a first arm and a second arm,
   the first arm providing the base and having the first row of spaced-apart holes disposed therein,
   the second arm having the second row of spaced-apart holes disposed therein,
   the relative positions of the first and second support rods being adjustable by selection of holes through which the support rods extend,
   the side members and support rods being formed from a corrosion-resistant material.

2. The apparatus of claim 1, wherein the corrosion-resistant material is a transparent plastic.

3. The apparatus of claim 1, the relative positions of the support rods being adjustable so as to support a test piece at an angle of approximately 30 degrees to the vertical.

4. The apparatus of claim 3, the holes selected from the first row of spaced-apart holes for each side member and the holes selected from the second row of spaced-part holes for each side member being selectable so as to obtain a desired orientation of the test piece when the test piece is supported by the apparatus.

5. The apparatus of claim 1, the support rods being generally cylindrical and extending through selected circular holes in the side members.

6. An apparatus, the apparatus comprising:
   a first side member;
   a second side member;
   a first support rod; and
   a second support rod,
   the first and second side members having a similar form,
      each side member having a generally L-shaped form having a first arm and a second arm, the first arm providing a base and having a first row of spaced-apart holes disposed therein, the second arm having a second row of spaced-apart holes disposed therein,
   the first and second side members being connectable by the support rods so that the first support rod extends between holes selected from the first row of spaced-apart holes of each side member, and the second support rod extends between holes selected from the second row of spaced-apart holes for each side member,
   the apparatus being a support stand for supporting a test piece within a corrosion chamber,
   the orientation of the test piece being adjustable through selecting holes between which the support rods extend,
   the side members and support rods being formed from a corrosion-resistant material.

7. The apparatus of claim 6, the first and second side members having a similar form and similar spatial distribution of holes therein
   the first arm and the second arm of each side member having a square or rectangular cross-section,
   the spaced apart holes being oriented generally normal to the plane of the L-shape.

8. A method of corrosion testing a test piece within a corrosion chamber, the test piece being a vehicle panel, the test piece including a test surface, the method comprising:
   providing a support stand within the corrosion chamber, the support stand including a pair of side members, a first support rod, and a second support rod,
   each of the pair of side members being generally L-shaped,
   the side members and support rods being formed from a corrosion-resistant material,
   the support rods being disposed between the pair of side members, at least one support rod having an adjustable position;
   placing the test piece on the support stand, the adjustable position being selected so that the test surface has a desired orientation; and
   corrosion testing the test piece with the test surface at the desired orientation.

9. The method of claim 8, wherein the test piece has at least one dimension greater than 1 meter.

10. The method of claim 8, both support rods having an adjustable position.

* * * * *

UNITED STATES PATENT AND TRADEMARK OFFICE
CERTIFICATE OF CORRECTION

PATENT NO. : 8,161,804 B2  
APPLICATION NO. : 12/480274  
DATED : April 24, 2012  
INVENTOR(S) : Herdzik et al.

Page 1 of 1

It is certified that error appears in the above-identified patent and that said Letters Patent is hereby corrected as shown below:

In the Specification

Col. 1, line 40: replace "second aim" with --second arm--;

Col. 6, line 10: replace "jean" with --lean--.

Signed and Sealed this  
Twenty-sixth Day of November, 2013

Margaret A. Focarino  
*Commissioner for Patents of the United States Patent and Trademark Office*